United States Patent [19]

Antocci et al.

[11] Patent Number: 5,266,268
[45] Date of Patent: Nov. 30, 1993

[54] CENTRIFUGAL ANALYZER ROTORS

[75] Inventors: Joseph D. Antocci, Leominster; Richard H. Darling, Andover; Maxwell E. Lawrence, Jr., Waltham; Joseph A. Luongo, Walpole, all of Mass.

[73] Assignee: Iniziative Maritime 1991, S.R.L., Turin, Italy

[21] Appl. No.: 745,520

[22] Filed: Aug. 15, 1991

[51] Int. Cl.$^5$ .................. G01N 21/90; G01N 1/10
[52] U.S. Cl. ........................ 422/72; 422/102; 422/63; 422/64; 436/45; 436/47; 436/177
[58] Field of Search .............. 422/72, 102, 63, 64; 436/45, 47, 177; 494/16, 34; 356/246

[56] References Cited

U.S. PATENT DOCUMENTS

| | | | |
|---|---|---|---|
| 4,226,531 | 10/1980 | Tiffany et al. | 356/246 |
| 4,314,970 | 2/1982 | Stein et al. | 422/72 |
| 4,373,812 | 2/1983 | Stein et al. | 422/72 X |
| 4,387,164 | 6/1983 | Hevey et al. | 436/45 |
| 4,387,992 | 6/1983 | Swartz | 356/246 |
| 4,566,790 | 1/1986 | Mandle | 356/246 |
| 4,580,896 | 4/1986 | Brickus et al. | 356/246 |
| 4,580,897 | 4/1986 | Nelson et al. | 356/246 |
| 4,656,009 | 4/1987 | Benajam | 422/102 |
| 4,726,683 | 2/1988 | Nebuloni | 422/72 |
| 4,777,141 | 10/1988 | Calzi et al. | 436/69 |
| 4,902,497 | 2/1990 | Brickus | 422/72 |

*Primary Examiner*—Lyle A. Alexander
*Attorney, Agent, or Firm*—Fish & Richardson

[57] ABSTRACT

A multicuvette rotor which reduces unacceptable tendencies of reagent or a sample material to spontaneously move or "wick" from one chamber compartment to the other, resulting in premature conmingling of reactants, and of sample or reagent material to flow out of one or more of the radially outer loading ports during acceleration of the rotor for transfer of the sample or reagent material from inner chambers to corresponding outer chambers.

14 Claims, 2 Drawing Sheets

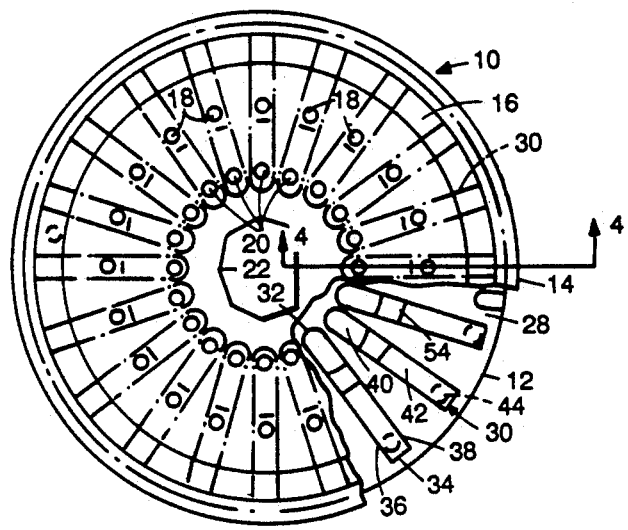
FIG. 1
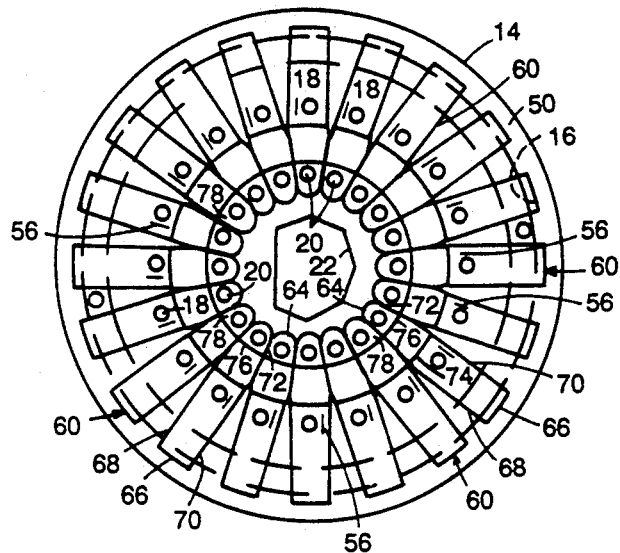
FIG. 2
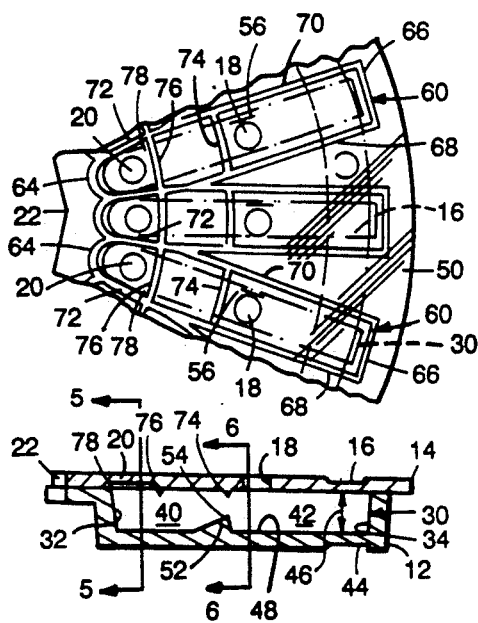
FIG. 3
FIG. 4

CENTRIFUGAL ANALYZER ROTORS

This invention relates to analytical systems, and more particularly to cuvette rotors for use in automated centrifugal analyzer systems and the like.

Centrifugal analyzers are useful in performing a variety of analyses, including kinetic and endpoint analyses, by such techniques as absorption, light scattering and fluorescence. Such analyzers are commonly used in the analysis of biological fluids such as blood, blood plasma or serum components, and perform blood coagulation measurements, absorbance mode analyses for glucose, cholesterol, creatinine, total protein, calcium, phosphorous, enzymes, and the like, and fluorescence or light scattering mode analyses for glucose, bile acids, phenytoin, theophylline, gentamycin and the like.

In general, such analyzers utilize a multicuvette rotor assembly which has a circumferential array of spaced elongated radially extending cuvettes, each of which has an inner chamber for initially holding a first reactant which frequently is a sample of blood or other biological fluid, and an outer chamber for initially holding one or more different reactants. Divider structure such as a ramp separates the two chambers, and reactants are transferred by centrifugal force to an analysis region at the outer end of the cuvette for mixing and reaction and subsequent analysis of the reaction by photometric or other analysis technique. Such rotors may be of the reusable type, as disclosed in Stein et al. U.S. Pat. No. 4,314,970 for example or of the disposable type as disclosed in Tiffany et al. U.S. Pat. No. 4,226,531, Brickus et al. U.S. Pat. No. 4,580,896, Nelson et al. U.S. Pat. No. 4,580,897, Nebuloni U.S. Pat. No. 4,726,683 or Brickus U.S. Pat. No. 4,902,497 for example. To achieve desired analysis accuracies, the rotor must have precise and stable dimensional accuracies that are uniform between the several cuvettes of the rotor; the reactants must be sufficiently isolated to prevent premature conmingling; and reactant material should not be discharged from the rotor during centrifugal transfer, for example.

In a typical processing sequence, the rotor assembly is accelerated for combining sample and reagent, then braked for further mixing, and then brought up to about a speed of about 1,000 rpm for photometric and/or fluorescence analysis. Intermediate incubation intervals may be employed, and additional reagents may be added after initial mixing. For example, in a coagulation assay of the type described in Calzi U.S. Pat. No. 4,777,141, the disclosure of which is expressly incorporated herein by reference, a two reagent cycle may be employed in which a plasma sample is loaded into an inner cuvette chamber and a first (coagulation activating) reagent is simultaneously loaded into the corresponding outer chamber of the cuvette; after the cuvettes of the rotor have been loaded, the rotor is spun to cause the plasma samples to flow over the ramps and mix with the reagents in the outer chambers. After mixing, the rotor is stopped and a second (coagulation initiating) reagent is sequentially loaded into the inner chambers of the cuvettes over an interval of several minutes. After the loading of the second reagents is complete, the rotor is again spun to cause the second reagent to flow over the ramps where it mixes with plasma already mixed with the first reagent and a coagulation reaction is initiated. Radiation from a light source is passed through the end surface of the rotor and a light scattering measurement are taken to monitor the clot formation processes in the several cuvettes. As the clot formation process is initiated by conmingling of the plasma sample and the second reagent, it is essential for accuracy of the measurement that there not be any premature mixing of the plasma and second reagent. It has been found that there is an unacceptable tendency for reactant (reagent or sample) material to spontaneously move or "wick" along the region between the upper surface of the cuvette and the side wall of the cuvette adjacent the junction between the cover and body members, resulting in premature initiation of the coagulation reaction and thereby distorting the accuracy of the clot formation measurement.

The invention, in one aspect, provides a multicuvette rotor which reduces an unacceptable tendency of reagent or a sample material to spontaneously move or "wick" from one chamber compartment to the other, resulting in premature conmingling of reactants. The invention, in another aspect, provides a multicuvette rotor in which a tendency of sample or reagent material to flow out of one or more of the radially outer loading ports during acceleration of the rotor for transfer of the sample or reagent material from inner chambers to corresponding outer chambers is reduced. Such discharge creates contamination in regions adjacent the rotor.

In accordance with an aspect of the invention, there is provided a multicuvette rotor for use in a centrifugal analyzer in which a circumferential array of elongated radially extending cuvettes are defined. Each elongated cuvette has a ceiling surface and defines a first chamber region for receiving a first reactant and a loading port in the ceiling surface through which a first reactant is introduced into the first chamber region, a second chamber region for receiving a second reactant and a second loading port in the ceiling surface through which a second reactant is introduced into the second chamber region, and a ramp surface with a ramp crest spaced from the ceiling surface of the cuvette so that a transfer passage between the first and second chamber regions is defined through which the first reactant may be flowed into the second chamber region for forming a reaction product with the second reactant. A generally radially disposed guide channel is in the cuvette ceiling surface between each radially outer loading port and the adjacent trailing (in the direction of rotation) sidewall and extends past that port. An analysis region is defined adjacent the radially outer wall of the cuvette where the resulting reaction product is subjected to analysis.

In accordance with another aspect of the invention, there is provided a multicuvette rotor for use in a centrifugal analyzer in which a circumferential array of elongated radially extending cuvettes are defined. Continuous seal structure extends around each cuvette recess between an upper surface of a body member and a lower surface of a cover member. Each elongated cuvette defines a first chamber region for receiving a first reactant and a radially inner loading port through which a first reactant is introduced into the first chamber region, a second chamber region for receiving a second reactant and a radially outer loading port through which a second reactant is introduced into the second chamber region, and a ramp surface with a ramp crest spaced from the ceiling surface of the cuvette so that a transfer passage between the first and second chamber regions is defined through which the first reactant may be flowed into the second chamber region for forming a reaction product with the second reactant. At the top of each first chamber region, in the seal region adjacent each radially inner loading port a recess of greater than capillary dimension is provided in the intersection region of the cuvette ceiling and sidewalls. An analysis region is defined adjacent the radially outer wall of each cuvette where the resulting reaction product is subjected to analysis.

In a particular embodiment, the rotor has a diameter of about ten centimeters and an overall height of about one centimeter, and defines twenty analysis cuvettes. The rotor includes a one-piece body member of transparent material that has a planar upper surface and that defines a circumferential array of elongated cuvette recesses, and a one-piece cover member of transparent material that has a planar lower seal surface parallel to the planar upper seal surface of the body member with a continuous seal extending around each cuvette recess between the planar upper and lower surfaces to define the circumferential array of analytical cuvettes. The seal is formed of melted energy director ridge material that extends about the periphery of each cuvette. Barrier structure of melted plastic material merges with the melted energy director ridge material and obstructs a channel of capillary dimension that extends along the upper edge of a sidewall of a cuvette adjacent the junction between the cover and body members. Each cuvette of that rotor has a length of about three centimeters; its planar top (ceiling) and bottom (floor) walls are spaced apart about ⅜ centimeter in the analysis and chamber regions, and the analysis and chamber region side walls are parallel and spaced about five millimeters apart. The loading ports for the inner cuvette chambers are about three millimeters in diameter and are disposed in circumferential array and the ceiling surface surrounding each such inner loading port is spaced at least about 0.4 millimeter above the upper seal surface of the body member and extends to a point immediately adjacent the energy director ridge seal portion. The loading ports for the outer cuvette chambers are also about three millimeters in diameter and are disposed in an outer circumferential array spaced about 1.5 centimeters on center from the array of inner chamber loading ports. The guide channel structure in that embodiment has a width at the ceiling surface of about one-third millimeter, a depth of about one-quarter millimeter, is spaced about 0.2 millimeter from the outer loading port, and extends a length of about five millimeters along the ceiling surface between the outer loading port and the sidewall that trails in the direction of rotation. The rotor also defines a series of optical cuvette end windows that are transparent at analytical wavelengths; the length of the optical path in the analysis region is greater that the circumferential width or radial length of the analysis region; and the volume of each of the first and second chambers is greater than that of the analysis region.

The invention provides compact, economical centrifugal analyzer rotors that may be of the single use type with capability for increased throughput and reduced cost per analysis that are compatible with automated rotor handling equipment, that reduce an unacceptable tendency of reagent or a sample material to spontaneously move or "wick" from one chamber compartment to the other, resulting in premature mixing of reactants; and that reduce a tendency of sample or reagent material to flow out of one or more of the radially outer loading ports during acceleration of the rotor for transfer of the sample or reagent material from inner chambers to corresponding outer chambers.

Other features and advantages of the invention will be seen as the following description of a particular embodiment progresses, in conjunction with the drawings, in which:

FIG. 1 is a top plan view (with portions broken away) of a multicuvette rotor assembly in accordance with the invention;

FIG. 2 is a plan view showing the bottom face of the cover member of the rotor assembly shown in FIG. 1;

FIG. 3 is an enlarged view of a portion of that cover member;

FIG. 4 is a sectional view taken along the line 4—4 of FIG. 1;

DESCRIPTION OF PARTICULAR EMBODIMENT

Figure 5:
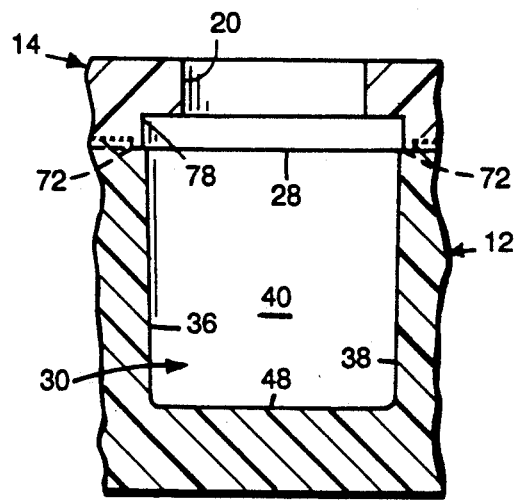
FIG. 5 is a sectional view taken along the line 5—5 of FIG. 4.
Figure 6:
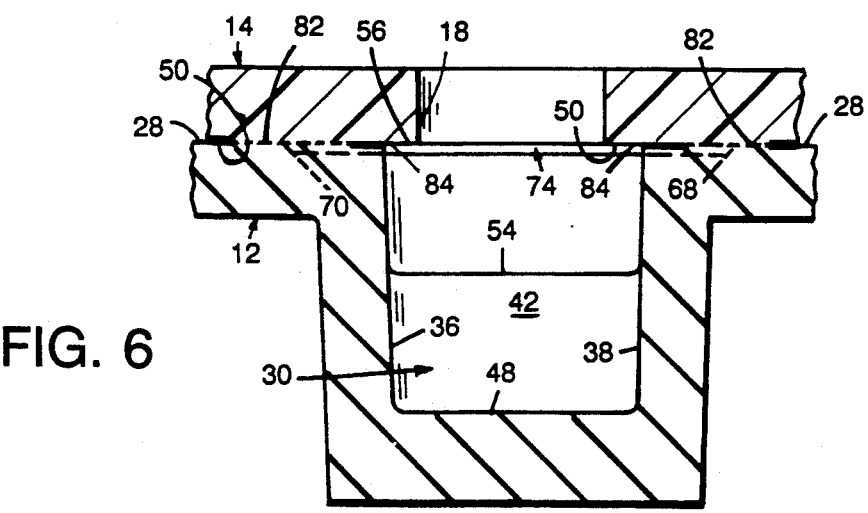
FIG. 6 is a sectional view taken along the line 6—6 of FIG. 4.

The rotor assembly 10 shown in FIG. 1 has a diameter of about ten centimeters and an overall height of about three-quarter centimeter and is formed of an injection molded acrylic body member 12 and an injection molded acrylic cover member 14 and has the desired transparency, chemical resistance, and optical characteristics for photometric analysis. The cover member 14 is a flat circular disc that has an optical window channel 16, a circumferential array of outer loading ports 18, a circumferential array of inner loading ports 20, and central opening 22.

Body member 12 has a planar upper surface 28 and a circumferential array of twenty individual cuvette recesses 30, each of which has a length of about four centimeters between a cylindrical inner wall 32 and a planar outer wall 34; and a width of about 0.45 centimeter between planar trailing sidewall 36 and parallel planar leading side wall 38. Each cuvette 30 has an inner chamber 40 which is loaded through port 20 and an outer chamber 42 which is loaded through port 18. Formed in the base of chamber 42 is a recessed optical window 44 aligned with optical channel 16 to provide an analysis region 46 that has an optical path length of one-half centimeter between cuvette base surface 48 and the parallel inner (ceiling) surface 50 of cover 14. In each cuvette 30, as indicated in FIG. 4, is divider ramp structure 52 that has a radial length of about six millimeters, a crest 54 that has a height of about one quarter centimeter, a planar inclined ramp surface that forms the rear wall of cuvette chamber 40 and a planar vertical surface that forms the inner wall of cuvette chamber 42, with chamber 42 having a static capacity of about 250 microliters.

Further details of cover member 14 may be seen with reference to FIGS. 2-6. Member 14 is a disc that has a diameter of about ten centimeters and a thickness of about 1.25 millimeters. Disc 14 has planar lower surface 50 on which is formed a radially extending guide channel 56 adjacent each outer loading port 18; and an array of perimeter energy director ridges 60, each of which extends about the perimeter of an individual cuvette 30, as indicated in FIG. 3. Each guide channel 56 is of triangular cross sectional configuration (FIG. 6), has a depth of about one-quarter millimeter, a width of about one-third millimeter, and a length of about one-half centimeter, is spaced about 0.2 millimeter from port 18, and its radially inner end is rearwardly of ramp crest 54 and about one millimeter radially inward of outer loading port 18. Each perimeter ridge 60 is of triangular cross-sectional configuration with a height of about 0.3 millimeter and a base width of about 0.5 millimeter; and includes arcuate inner wall section 64, outer wall section 66, parallel sidewall sections 68, 70, spaced apart about 0.7 centimeter and shared sidewall section 72. A first set of barrier ridges 74 extends between the energy director sidewall ridges 68, 70 at a radius of about three centimeters, ridge 74 being located about one-quarter centimeter radially inwardly from outer loading port 18. A second set of barrier ridges 76 (essentially in the form of a ring that merges with the common wall portions 72 of perimeter ridge 60) is located at a radius of about two centimeters (spaced about one millimeter radially outwardly from inner loading port 20). Further details of the perimeter ridges 60 and the barrier ridges 74, 76 may be had with reference to U.S. Pat. No. 4,902,479. A recess 78, (FIG. 5) about 0.4 millimeter deep, is formed in surface 50 surrounding each inner port 20 in the region bounded by arcuate inner ridge section 64, shared sidewall ridge sections 72, and barrier ridge section 76.

In sealing cover 14 to body 12, cover 14 is placed on the upper surface of body 12 with the crests of the peripheral ridges 60 resting on body surface 28 such that cover surface 50 is spaced about 0.3 millimeter from body surface 28. Cover 14 is then ultrasonically welded to body 12 with a horn pressure of about sixty psi and application of twenty kilohertz energy for about one second. That ultrasonic energy melts the energy director ridges 60 and creates a peripheral seal (as indicated at 82 in FIGS. 5 and 6) about each cuvette 30. The melted plastic material flows along surfaces 28 and 50 but frequently a capillary gap 84 (FIG. 6) (typically less than 0.1 millimeter in width) remains between cover surface 50 and body surface 28 adjacent cuvette side wall 36, 38. The barrier ridges 74, 76 are also melted during the ultrasonic welding in those regions where they overlie body surface 28 producing a weld type merger of plastic material that fills and obstructs each crevice area 84 with each barrier ridge 74, 76 of each cuvette 30 extending from each merger area across the entire width of the cuvette between the cuvette sidewalls 36, 38. Due to cover recess 78 (FIG. 5), there is no capillary gap 84 radially inward of barrier ridge 76, the 0.4 millimeter width of that recess being substantially greater than capillary dimension.

Thus, while reagent material may rapidly wick by capillary action along channel 84, each such channel is blocked by the melted merged portions of the barrier ridges 74, 76. These barrier structures thus inhibit spontaneous premixing of regent materials by flow either along the cover surface 50 or along a channel 84 from one chamber 40, 42 to the other. Further, due to recess 78, there is no capillary action supporting gap 84 radially inward of ridge 76.

Figure 7:
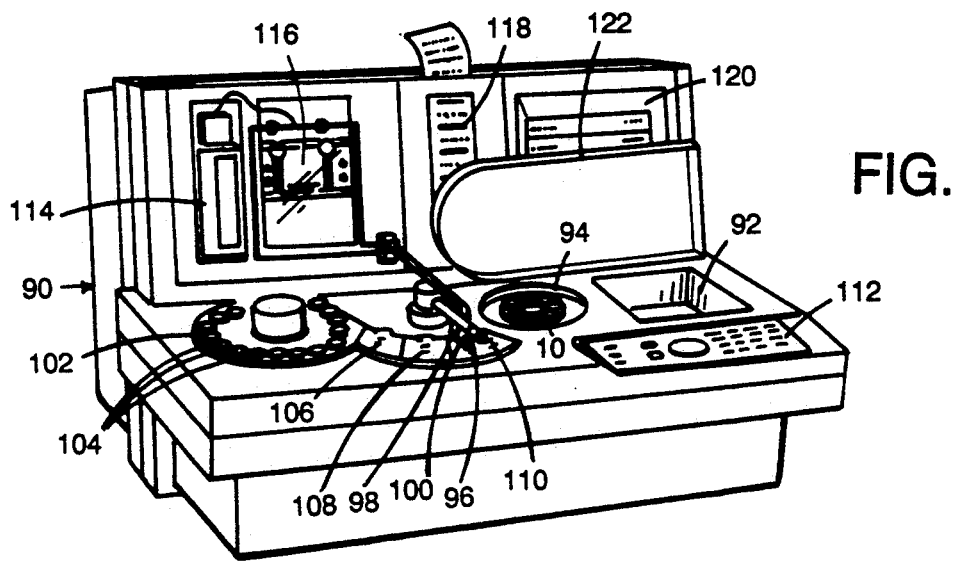
FIG. 7 is a view of a microcentrifugal analyzer that uses rotors of the type shown in FIGS. 1-6.

With reference to FIG. 7, a micro centrifugal analyzer system 90 has rotor preheater chamber 92, analysis station 94 that receives rotor 10 and transport arm 96 that carries two pipette tubes 98, 100. A sample tray 102 positions twenty sample cups 104; and reagent reservoirs 106, 108, and rinse reservoir 110 are positioned between sample tray 102 and analysis station 94 along the path of transport arm 96. Samples, standards, and controls are placed in the sample cups 104 and reagents are in the reagent reservoirs 106, 108. Analyzer control selections are made by entries on control keyboard 112. Also mounted on the analyzer are reference solution supply 114, dilutor 116, thermal printer 118, and video display unit 120.

In this embodiment, a selected volume of plasma from a sample cup 104 is dispensed into the chamber 40 and a selected volume of a coagulation activating reagent from reservoir 106 is dispensed into chamber 42 of a cuvette of rotor 10 at analysis station 94. As indicated above, as the sample and reagent volumes flow into their respective cuvettes, a drop of the dispensed liquid may adhere to the edge of the loading port, and/or the wetted gap or channel 84 between cover 14 and body 12 may tend to draw liquid in capillary wicking action back to chamber 40 and prematurely initiate clot formation due to mixing with the second reagent in inner chambers 40. Any such wicking action between chambers 40 and 42, however, is inhibited by the barrier structures 74, 76 and the absence of a capillary gap radially inward of barrier 76 such that spontaneous mixing of reagents due to such capillary wicking action between the two chambers of a cuvette is effectively prevented.

After the twenty cuvettes 30 of rotor 10 have been loaded, cover 122 is closed and the rotor 10 is centrifugally accelerated at analysis station 94 to transfer plasma samples from chambers 40 to analysis chambers 42 and mixing with the coagulation activating reagents. The plasma sample is forced against trailing sidewall 36 during this centrifugally accelerated flow to analysis chamber 42, and guide channel 56 guides that flow radially outward so that reactant material is not discharged from port 18.

The rotor 10 is then braked and the mixtures of samples and reagents in the outer chambers 42 are incubated while transport arm 96 loads a second (coagulation initiating) reagent from reservoir 108 into the inner chambers 40. After loading of the second reagent is complete, the rotor is then accelerated again to transfer the second reagent from chamber 40 to analysis chambers 42 for mixing and initiation of the coagulation reaction Which is monitored by light scattering as the rotor is spinning. Data acquisition continues for a period greater than the longest time expected for coagulation, for example, two to four minutes. Measurement is individual for each cuvette, and the light scatter value is displayed by video display unit 120 and may be printed out by thermal printer 118.

In a test of rotors with and without channels 56, discharge of reactant material through ports 18 was reduced over ninety percent through the provision of channels 56. In a similar test of rotors with and without recesses 78, premature initiation of coagulation reactions (false trip) was completely eliminated through the provision of recesses 78.

While a particular embodiment of the invention has been shown a described, various modifications will be apparent to those skilled in the art, and therefore it is not intended that the invention be limited to the disclosed embodiment or to details thereof a departures may be made therefrom within the spirit and scope of the invention.

What is claimed is:

1. A multicuvette rotor for use in a centrifugal analyzer comprising a body member and a cooperating cover member defining a circumferential array of elongated radially extending cuvettes, a continuous seal structure extending around each said cuvette between an upper surface of said body member and a lower surface of said cover member, each said elongated cuvette defining a first chamber region for receiving a first reactant and a radially inner loading port through which a first reactant is introduced into said first chamber region, second chamber region for receiving a second reactant and a radially outer loading port through which a second reactant is introduced into said second chamber region, and a ramp surface with a ramp crest spaced from the lower surface of said cover member, said ramp surface being disposed between said first and second chamber regions so that a transfer passage between said first and second chamber regions is defined through which the first and second chamber into said second chamber region for forming a reaction product with the second reactant, a recess structure at the top of each said first chamber region surrounding each said radially inner loading port and adjacent said seal structure, said recess structure defining a recess of at least about 0.4 millimeter depth in the intersection region of said lower surface of said cover member and sidewalls of each said cuvette, and a structure defining an analysis region adjacent a radially outer wall of each said cuvette where the resulting reaction product is subjected to analysis.

2. The rotor of claim 1 wherein said recess of said cover member surrounding each said inner loading port extends to a point immediately adjacent said seal structure.

3. The rotor of claim 1 wherein said continuous seal structure is formed of melted energy director ridge material.

4. The rotor of claim 3 and further including barrier structure of melted plastic material which merges with said melted energy director ridge material and obstructs a channel of capillary dimension that extends along an upper edge of a sidewall of each said cuvette adjacent said seal structure.

5. A multicuvette rotor for use in a centrifugal analyzer, said rotor defining a circumferential array of elongated radially extending cuvettes and comprising a one-piece body member of transparent material that has a planar upper surface and that defines a circumferential array of elongated cuvette recesses, each said cuvette recess having spaced side walls, and a one-piece cover member of transparent material that has a planar lower surface parallel to said planar upper surface of said body member, continuous seal structure extending around each said cuvette recess between said planar upper and lower surfaces at a junction between said body and cover members to define said circumferential array of analytical cuvettes, each said elongated cuvette recess including structure defining a first chamber region for receiving a first constituent and a radially inner loading port in said cover member through which a first constituent may be introduced into said first chamber region, structure defining a second chamber region for receiving a second constituent and a radially outer loading port in said cover member through which a second constituent may be introduced into said second chamber region, structure defining a radially outer wall of said second chamber region, recess structure at the top of each said first chamber region adjacent each said radially inner loading port, said recess structure defining a recess of greater than capillary dimension in the intersection region of the lower surface of said cover member and sidewalls of each said cuvette recess, said seal structure further including barrier structure in each cuvette recess, each said barrier structure being connected to said lower surface of said cover member and located between the loading ports of said first and second chamber regions and extending from said seal structure at least to the sidewall of said cuvette recess adjacent said junction between said cover and body members for inhibiting wicking movement along said cover member of a constituent stored in one of said chamber regions to the other chamber region and premature mixing of constituents stored in said cuvette recesses, and divider structure between said first and second chamber regions in each cuvette recess, each said divider structure being connected to a bottom wall of said cuvette recess and having a crest portion spaced from said lower surface of said cover member so that a transfer passage between said first and second chamber regions is defined between said crest portion and said lower surface of said cover member through which a constituent may be flowed into said second chamber region for forming a reaction product with a second constituent, structure defining a generally radially disposed guide channel in said lower surface of said cover member between each said radially outer loading port and an adjacent trailing sidewall rotation of said cuvette recess in the direction of rotation of said outer, each said guide channel extending from a point radially inward of each said radially outer loading port past each said radially outer loading port to a point radially outward of said radially outer loading port, and structure defining an analysis region adjacent the radially outer wall of each said cuvette recess where the resulting reaction product is subjected to analysis.

6. The rotor of claim 5 wherein said seal structure includes melted energy director ridge material that extends about each said cuvette recess.

7. The rotor of claim 6 wherein said cover member is a flat circular disk that has an optical window region adjacent an outer periphery thereof, an outer circumferential array of loading ports, an inner circumferential array of loading ports, and means defining a central opening.

8. The rotor of claim 7 and further including barrier structure of melted plastic material that merges with said melted energy director ridge material and obstructs a channel of capillary dimension that extends along an upper edge of a sidewall of each said cuvette recess adjacent the junction between said cover and body members.

9. The rotor of claim 8 wherein each said cuvette recess has a length of about three centimeters; and lower surface of said cover member and said bottom wall of said cuvette recess are spaced apart about $\frac{3}{4}$ centimeter in said analysis and chamber regions, and the sidewalls of said analysis and chamber regions are parallel and spaced about five millimeters apart.

10. The rotor of claim 9 wherein each said loading port is about three millimeters in diameter.

11. The rotor of claim 10 wherein the lower surface of said cover member surrounding each said inner loading port is spaced at least about 0.4 millimeter above the upper surface of said body member and extends to a point immediately adjacent said seal structure.

12. The rotor of claim 11 wherein said outer chamber loading ports are disposed in an outer circumferential array spaced at least about one centimeter on center from the circumferential array of said inner chamber loading ports.

13. The rotor of claim 12 wherein said guide channel structure has a width at said lower surface of said cover member of at least about one-quarter millimeter, a depth of at least about one-quarter millimeter, is spaced at least about 0.1 millimeter from the outer loading port, the radially inner end of said guide channel is rearwardly of said divider crest and said guide channel extends a length of at least about five millimeters along said lower surface of said cover member between the adjacent outer loading port and the sidewall that trails in the direction of rotation of said rotor.

14. The rotor of claim 13 and further including structure defining a series of optical cuvette end windows that are transparent at analytical wavelengths; the length of the optical path in said analysis region is greater that the circumferential width or radial length of the analysis region; and the volume of each of said first and second chamber regions is greater than that of said analysis region.

* * * * *